(12) United States Patent
Magnusson

(10) Patent No.: US 10,137,446 B2
(45) Date of Patent: Nov. 27, 2018

(54) DISPENSING DEVICE AND METHOD OF USE FOR DISPENSING A DEFINED VOLUME OF A LIQUID

(71) Applicant: Gunnar Magnusson, Årsta (SE)

(72) Inventor: Gunnar Magnusson, Årsta (SE)

(*) Notice: Subject to any disclaimer, the term of this patent is extended or adjusted under 35 U.S.C. 154(b) by 0 days.

(21) Appl. No.: 15/517,283

(22) PCT Filed: Sep. 30, 2015

(86) PCT No.: PCT/IB2015/057499
§ 371 (c)(1),
(2) Date: Apr. 6, 2017

(87) PCT Pub. No.: WO2016/055912
PCT Pub. Date: Apr. 14, 2016

(65) Prior Publication Data
US 2017/0246623 A1  Aug. 31, 2017

Related U.S. Application Data

(60) Provisional application No. 62/061,125, filed on Oct. 7, 2014, provisional application No. 62/100,167, filed on Jan. 6, 2015.

(51) Int. Cl.
*B01L 1/00* (2006.01)
*B01L 3/02* (2006.01)
(Continued)

(52) U.S. Cl.
CPC ........ *B01L 3/0224* (2013.01); *B01L 3/0217* (2013.01); *G01N 1/14* (2013.01); *B01L 3/02* (2013.01);
(Continued)

(58) Field of Classification Search
CPC ............. B01L 3/02; B01L 3/021; B01L 3/022
See application file for complete search history.

(56) References Cited

U.S. PATENT DOCUMENTS 3,757,585 A  9/1973  Hall et al.
4,263,257 A  4/1981  Metsaelae
(Continued)

FOREIGN PATENT DOCUMENTS

EP  0409650 A2  1/1991
FR  2727670 A1  6/1996

OTHER PUBLICATIONS

International Search Report of PCT/IB2015/057499, the whole document.
(Continued)

*Primary Examiner* — Jyoti Nagpaul
(74) *Attorney, Agent, or Firm* — CUSPA Technology Law Associates; Yi Li

(57) ABSTRACT

A dispensing device for dispensing a defined volume of a liquid from a closed container includes a housing and a spring loaded piston disposed therein. The housing has a holding chamber that includes chamber snap fit elements on the chamber wall, piston stop(s), and a bottom having a central opening with a tubular member extending therefrom. The spring loaded piston includes a push cap including snap fit arms extending from underside of a top pusher and a spring around a piston rod under the top pusher. The device is so configured that engagement modes between arm snap fit elements of the push cap and chamber snap fit elements of the holding chamber control a venting position and an injection starting position of the spring loaded piston, and abutment of the push cap with the piston stop(s) in the holding chamber controls an injection ending position of the spring loaded piston.

15 Claims, 7 Drawing Sheets

(51) Int. Cl.
*G01N 1/14* (2006.01)
*G01F 11/02* (2006.01)
*G01N 1/00* (2006.01)
*G01N 33/49* (2006.01)

(52) U.S. Cl.
CPC ..... *B01L 3/0296* (2013.01); *B01L 2200/0684* (2013.01); *B01L 2300/0672* (2013.01); *B01L 2300/0838* (2013.01); *B01L 2400/0478* (2013.01); *G01F 11/02* (2013.01); *G01N 1/00* (2013.01); *G01N 33/49* (2013.01)

(56) References Cited

U.S. PATENT DOCUMENTS

| | | | |
|---|---|---|---|
| 6,352,673 | B1 | 3/2002 | Rainin et al. |
| 6,403,037 | B1* | 6/2002 | Chang .................... B01L 3/502 |
| | | | 250/238 |
| 6,840,121 | B2* | 1/2005 | Thomas ................... G01N 1/14 |
| | | | 73/863.31 |
| 2010/0326214 | A1* | 12/2010 | Hornes ................... B01L 3/021 |
| | | | 73/864.01 |
| 2012/0160331 | A1 | 6/2012 | Egger-Clmenti et al. |
| 2016/0136637 | A1* | 5/2016 | Leckebusch .......... B01L 3/0217 |
| | | | 422/522 |

OTHER PUBLICATIONS

International Preliminary Report on Patentability of PCT/IB2015/057499, the whole document.

* cited by examiner

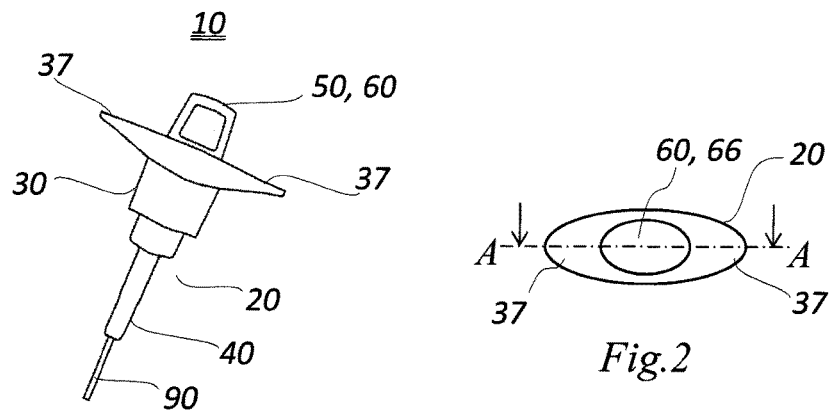
Fig.1
Fig.2
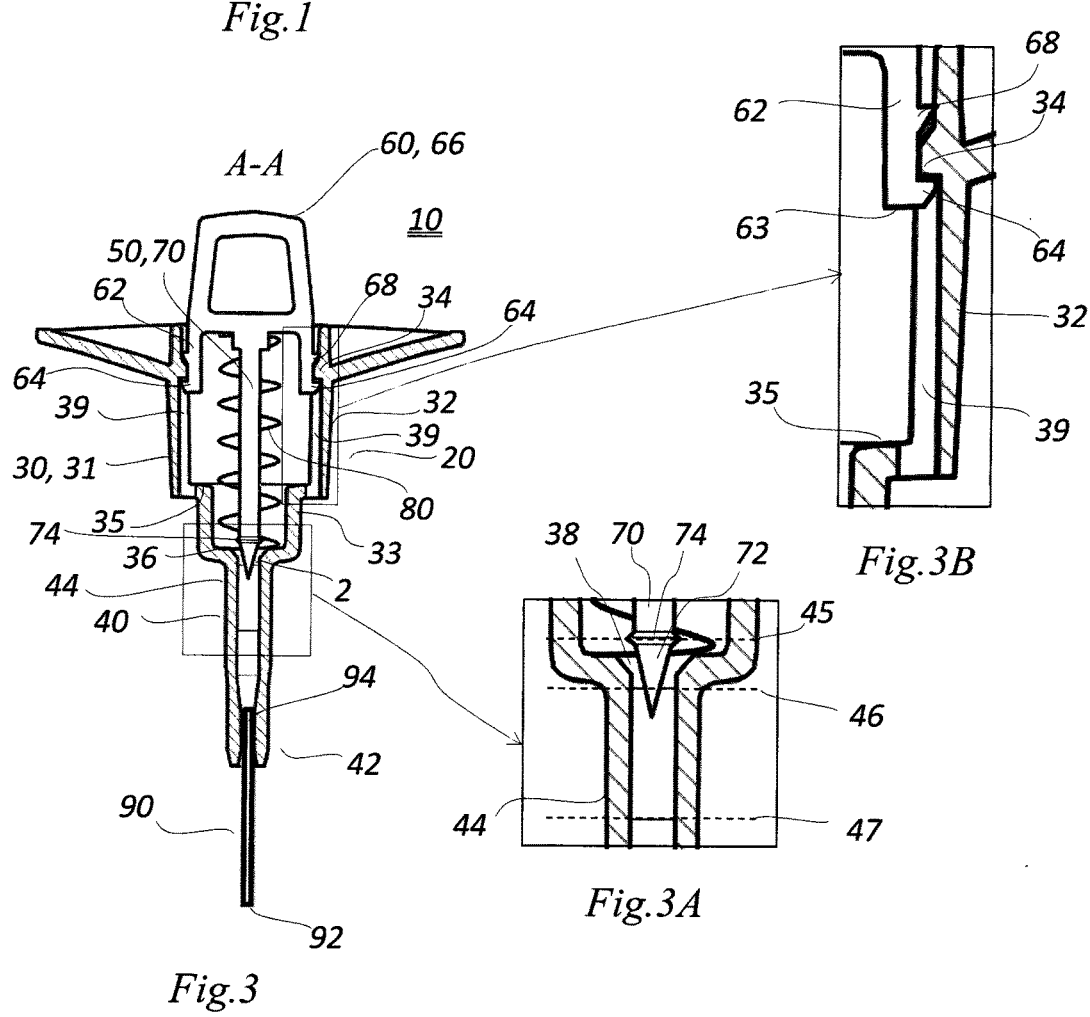
Fig.3B
Fig.3A
Fig.3

DISPENSING DEVICE AND METHOD OF USE FOR DISPENSING A DEFINED VOLUME OF A LIQUID

FIELD OF THE INVENTION

The present invention relates to a liquid dispensing device, more specifically relates to a manual liquid transferring and dispensing device and method of use for dispensing a defined volume of a liquid.

BACKGROUND OF THE INVENTION

A liquid biological sample such as blood is typically taken from a patient using a closed tube with vacuum, as commonly known as vacutainer. To transfer and dispense a volume of the liquid sample from the vacuum tube manually, the sealing cap of the vacuum tube can be removed and a volume of the liquid sample can be taken with a pipette. However, removing the cap of the vacuum tube involves biohazard risks, and shall be avoided whenever it is possible.

Several liquid sample transfer and dispense devices have been developed. One commonly used device in producing blood smear on a microscope slide is known as the Diff-Safe® blood dispenser manufactured by Alpha Scientific Corporation. This dispenser includes a needle in a holder. A sample is taken by penetrating the needle through the sealing cap of a vacuum tube. A droplet of the sample is dispensed on a microscope slide by reversing the vacuum tube and the holder together and placing the holder on the slide, and then pressing on the vacuum tube. The volume of a dispensed droplet is typically in a range from 5 to 30 µl, and the size of the droplet is proportional to the pressure applied on the vacuum tube. Therefore, the dispensed sample volume using such a device varies substantially and lacks accuracy and consistency.

On the other hand, a syringe can also be used for transferring a liquid sample from the vacuum tube. However, it is difficult to dispense an accurate and consistent volume manually with the syringe for a small volume of the sample. Moreover, the internal pressure of filled vacuum tubes varies depending on the extent of filling. This presents a problem when a syringe is used, because the uncontrolled pressure causes variation of the sample volume that is drawn from the filled vacuum tube. Furthermore, the sharp needle of a syringe is not preferred when it comes to operator's safety in handling biological samples.

Therefore, there is a need for an improved dispensing device that overcomes the above mentioned deficiencies.

SUMMARY OF THE INVENTION

In one aspect, the present invention is directed to a dispensing device for dispensing a defined volume of a liquid. In one embodiment, the dispensing device comprises a housing comprising a holding chamber comprising an open top, a chamber wall having one or more chamber snap fit elements on an interior thereof, one or more piston stops, and a bottom with a central opening, and a tubular member extending downward from the central opening on the bottom of the holding chamber; a cannula affixed to a distal segment of the tubular member; and a spring loaded piston. The spring loaded piston comprises a push cap disposed at least partially in the holding chamber, the push cap including a top pusher and at least one pair of snap fit arms extending downward from an underside of the top pusher; each of the snap fit arms including one or more arm snap fit elements complementary to the one or more chamber snap fit elements; a piston rod extending downward from the underside of the top pusher, coaxial with the central opening on the bottom of the holding chamber and the tubular member; and a spring disposed around the piston rod, with two opposing ends thereof against the underside of the top pusher and the bottom of the holding chamber, respectively; wherein the dispensing device is so configured that engagement modes between the one or more arm snap fit elements of the push cap and the one or more chamber snap fit elements of the holding chamber control a venting position and an injection starting position, respectively, of the spring loaded piston; and an abutment of at least one part of the push cap with the piston stop in the holding chamber controls an injection ending position of the spring loaded piston.

In a further aspect, the present invention is directed to a method of transferring a liquid from a closed container and dispensing a defined volume of the liquid using the dispensing device of the present invention. In one embodiment, the method comprises the steps of inserting the cannula of the dispensing device into a closed container that is in an upright position while the spring loaded piston is at a venting position wherein a piston head of the piston rod is so positioned that there is a venting space between the piston head and the central opening on the bottom of the holding chamber, and placing a distal end of the cannula in a head space above the liquid contained in the closed container, thereby establishing an air communication between the closed container and atmosphere through the central opening to release an internal pressure in the closed container; then pressing on the top pusher to irreversibly depart from a first engagement mode between the one or more arm snap fit elements of the push cap and the one or more chamber snap fit elements of the holding chamber, and to advance the push cap until the at least one part of the push cap abuts against the piston stop, thereby causing the spring loaded piston to move from the venting position through an injection starting position to an injection ending position, and resulting in injection into the closed container of a volume of air defined by a tubular volume in the tubular member between the injection starting and ending positions of the spring loaded piston; turning the closed container and the dispensing device together to an upside down orientation while maintaining the push cap pressed down; and then releasing the push cap and allowing the push cap to pull back automatically with the spring loaded piston returning to the injection starting position, thereby drawing the liquid into the cannula; removing the cannula out of the closed container; and then pressing on the top pusher until the at least one part of the push cap abuts against the piston stop, thereby dispensing a defined volume of the liquid, wherein the defined volume of the liquid is the tubular volume between the injection starting and ending positions of the spring loaded piston in the proximal segment of the tubular member.

The method further comprises steps for dispending another defined volume of the liquid from the closed container, which includes releasing the push cap after dispensing the first defined volume of the liquid described above and allowing air entering in the tubular member from the cannula; inserting the cannula of the dispensing device again into the closed container that is in the upright position, without pressing the top pusher of the dispensing device; then pressing on the top pusher until the at least a part of the push cap abuts against the piston stop, thereby causing the spring loaded piston to advance from the injection starting position to the injection ending position, and injecting into the closed container again of a volume of air defined by the tubular volume; and repeating the last three steps in dispensing the first defined volume of the liquid as described above to dispense another said defined volume of the liquid.

BRIEF DESCRIPTION OF THE DRAWINGS

FIG. 1 is a side view of the dispensing device according to one embodiment of the present invention, which is tilted as usually seen in manually dispensing a liquid.

FIG. 2 is a top view of the dispensing device shown in FIG. 1.

FIG. 3 is a cross sectional view of the dispensing device along line A-A in FIG. 2, with the spring loaded piston at a venting position; FIG. 3A is an enlarged view of a section around the bottom of the holding chamber and the proximal section of the tubular member of the dispensing device shown in FIG. 3; and FIG. 3B is an enlarged view of a section around the upper chamber wall of the holding chamber of the dispensing device shown in FIG. 3.

DETAILED DESCRIPTION OF THE INVENTION

Figures 3C, 3D, 3E:
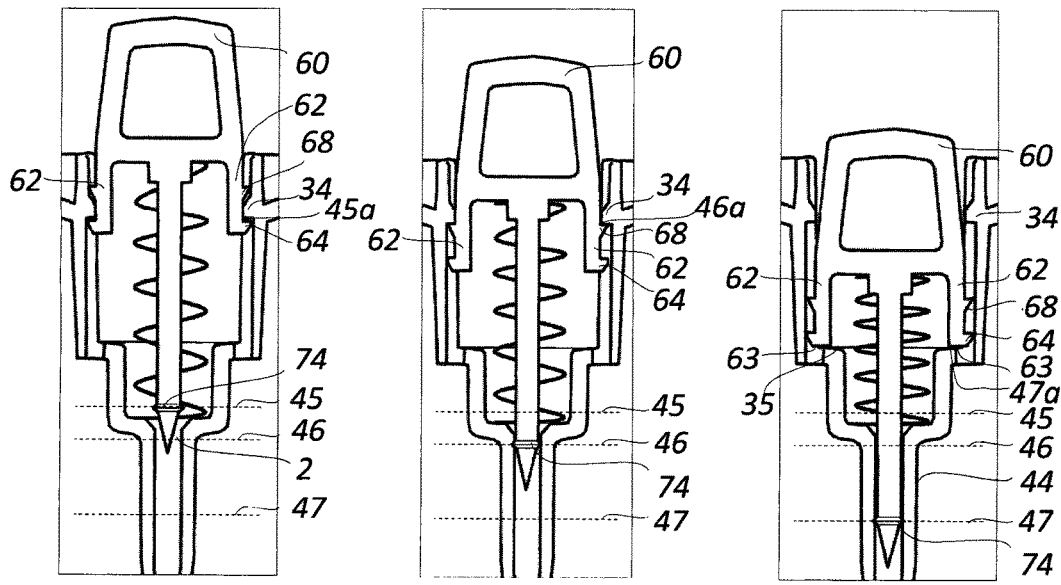
FIGS. 3C-3E are enlarged views of the holding chamber and the spring loaded piston with the piston head at different axial positions, wherein the cross sectional hatch lines are removed in order to show the line positions for visual clarity.

Embodiments of the present invention generally relate to a dispensing device for transferring a liquid from a closed container and dispensing a defined volume of the liquid. Embodiments of the invention are described more fully hereinafter with reference to the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

In some embodiments, the dispensing device comprises a housing including a holding chamber and a tubular member, a cannula, and a spring loaded piston. The holding chamber includes an open top, a chamber wall having one or more chamber snap fit elements on an interior thereof, one or more piston stops, and a bottom with a central opening. The tubular member extends downward from the central opening on the bottom of the holding chamber. The cannula is affixed to a distal segment of the tubular member.

The spring loaded piston includes a push cap disposed at least partially in the holding chamber, a piston rod and a spring. The push cap includes a top pusher and at least one pair of snap fit arms or a cap sidewall extending downward from an underside of the top pusher. Each snap fit arm, or the cap sidewall, includes one or more arm snap fit elements complementary to the one or more chamber snap fit elements on the chamber wall of the holding chamber for snap fit. The piston rod extends downward from the underside of the top pusher, coaxial with the central opening on the bottom of the holding chamber and the tubular member. The spring is disposed around the piston rod, with its two opposing ends against the underside of the top pusher and the bottom of the holding chamber, respectively.

The dispensing device is so configured that the engagement modes between the one or more arm snap fit elements of the push cap and the one or more chamber snap fit elements of the holding chamber control a venting position and an injection starting position, respectively, of the spring loaded piston, and that an abutment of at least one part of the push cap with the piston stop in the holding chamber controls an injection ending position of the spring loaded piston. In a first engagement mode between one or more arm snap fit elements of the push cap and one or more chamber snap fit elements of the holding chamber, the spring loaded piston is at the venting position at which the piston head of the piston rod is so positioned that there is a venting space between the piston head and the central opening on the bottom of the holding chamber. In a second engagement mode between one or more arm snap fit elements of the push cap and one or more chamber snap fit elements of the holding chamber, the spring loaded piston is at the injection starting position at which the piston head situates in the tubular member immediately below the central opening on the bottom of the holding chamber, and the piston head prohibits air communication between the tubular member and the holding chamber.

Referring now to the drawings, FIGS. 1 and 2 show a side view and a top view, respectively, of a dispensing device 10 in one embodiment of the present invention. In FIG. 1, the dispensing device is tilted as typically seen at the time of dispensing a liquid. FIG. 3 shows a cross sectional view of the dispensing device, along line A-A in FIG. 2. As shown, dispensing device 10 comprises a housing 20, a spring loaded piston 50, and a cannula 90. The housing 20 includes a holding chamber 30 and a tubular member 40 extending downward from holding chamber 30. The holding chamber 30 has an open top, an upper chamber portion 31 and a lower chamber portion 33. The upper chamber portion 31 has an upper chamber wall 32 that has one or more upper inner flanges 34 on the inner side, as the chamber snap fit elements (see FIGS. 3 and 3B). The one or more upper inner flanges 34 may be a continuous element along the chamber wall or may be in the form of separated elements disposed on opposing sides of the holding chamber as shown in FIG. 3. The lower chamber portion 33 has a bottom 36 with a central opening 38 (see FIG. 3A). In the embodiment shown in FIG. 3, the lower chamber portion has a smaller inner diameter than that of the upper chamber portion. As such, a stop platform 35 is formed at the low end of the upper chamber portion, which function as a piston stop as further described hereinafter. The lower chamber portion 33 has a height sufficient to house part of the spring when the spring loaded piston is at the injection ending position, where the spring is compressed. Alternatively, the lower chamber portion has the same inner diameter as that of the upper chamber portion, and piston stops are provided in the holding chamber as further described hereinafter.

The tubular member 40 extends integrally downward from central opening 38 on bottom 36 of holding chamber 30 and it has a distal segment 42 and a proximal segment 44. In the embodiment shown in FIGS. 3 and 3A, central opening 38 tapers downward and has a general cone shape. Alternatively, the central opening can also be straight without tapering, such as in a form of central opening 38a shown in FIG. 4.

As illustrated in FIGS. 3, 3A and 3B, spring loaded piston 50 includes a push cap 60, a piston rod 70 with a piston head 72, and a spring 80. The push cap 60 has a top pusher 66 and cap sidewall 62 in the form of two opposing snap fit arms 62 as shown in FIGS. 3 and 3B. The snap fit arms 62 include bottom outer lips 64 protruding on the outside, and upper snap fit lips 68 disposed above bottom outer lips 64 (see FIG. 3B). The distance between upper snap fit lips 68 and bottom outer lips 64 is complimentary to the height of upper inner flanges 34 of the upper chamber wall 32. Herein, the snap fit arms with upper snap fit lips 68 and bottom outer lips 64 are the snap fit elements of the push cap, and they assume two different engagement modes with the inner flanges 34 on chamber wall 32 of the holding chamber, as further described hereinafter.

As shown in FIGS. 3 and 3A, piston rod 70 extends downward from the underside of top pusher 66 and coaxially aligns with tubular member 40 of the housing, and piston head 72 is partially disposed in central opening 38 of holding chamber 30. The spring 80 is disposed around piston rod 70, with its two opposing ends against the underside of top pusher 66 of the push cap and bottom 36 of holding chamber 30, respectively. As can be seen more clearly in FIG. 3A, piston head 72 has a circumferential rim 74 that has an outer diameter complementary to the inner diameter of proximal section 44 of the tubular member 40. When rim 74 of the piston head moves into tubular member 40 during the use of the device, it prohibits air communication between the spaces above and below the rim 74. The axial position of the piston head as described hereinafter refers to the position of its rim 74 unless specified otherwise. Furthermore, in the embodiment shown in FIGS. 3 and 3A, piston head 72 has a conical distal end, which together with the cone shape of central opening 38 facilitates alignment and axial movement of the piston head in the central opening 38 of the holding chamber.

The push cap 60 of the spring loaded piston is slidingly movable in holding chamber 30, when a force is applied thereon or when the applied force is removed, which causes an axial movement of piston head 72. The extent of the sliding movement of push cap 60 is restricted at specific positions in the holding chamber 30, as controlled by the engagement modes between the bottom outer lips 64 and upper snap fit lips 68 with the inner flanges 34 of chamber wall 32, and the abutment of the push cap with the stop platform 35 of the holding chamber, which results in the axial movement of piston head 72 among distinct axial positions relative to the tubular member 40.

More specifically, as shown in FIG. 3C, at its assembled position of the push cap 60 before the use of the dispensing device, upper snap fit lips 68 are situated above upper inner flanges 34 on chamber wall 32 of the holding chamber, while bottom outer lips 64 of the push cap have been irreversibly snapped over the inner flanges 34, and the bottom outer lips 64 abut against upper inner flanges 34 of the chamber wall as driven by the force asserted by spring 80. Moreover, upper inner flanges 34 of chamber wall 32 restrict upper snap fit lips 68 from moving downward in the absence of force applied by the user on the top pusher. This is referred to as the first engagement mode between the lips 64 and 68 on snap fit arms 62 of the push cap and the inner flanges 34 on chamber wall 32 of the holding chamber. At this point, rim 74 of the piston head is disposed at line 45 above central opening 38 on bottom 36 of the holding chamber. At this position, there is a venting space 2 between piston head 72 and central opening 38, which establishes air communication between the interior of tubular member 40 and atmosphere through the holding chamber, because holding chamber 30 is not air sealed. Therefore, this position of the spring loaded piston is referred to as the venting position, and line 45 is also referred to as venting line. As shown in FIG. 3C, the venting position is controlled by the abutment between bottom outer lips 64 of the push cap and upper inner flanges 34 on the chamber wall of the holding chamber at the point 45a, or the first engagement mode referred above.

As shown in FIG. 3D, during the use of the dispensing device push cap 60 is pressed downward to cause upper snap fit lips 68 of the push cap to snap over upper inner flanges 34 of the chamber wall; however, at the position shown the upper snap fit lips 68 abut against upper inner flanges 34 as forced by spring 80, when no force is applied on the push cap by the user. This is referred to as the second engagement mode between the lips 64 and 68 of the push cap and the inner flanges 34 on chamber wall 32 of the holding chamber. At this point, rim 74 of the piston head is disposed in tubular member 40 at line 46 immediately below central opening 38 on bottom 36 of the holding chamber. At this position, rim 74 seals tubular member 40 and prohibits air communication between the tubular member and the holding chamber. As such, further pressing push cap 60 causes injection of a volume of air contained in tubular member 40 to a tube engaged with cannula 90, as further described in detail hereinafter. Therefore, this position of the spring loaded piston is referred to as injection starting position, and line 46 is also referred to as injection starting line. As shown in FIG. 3D, the injection starting position is controlled by the abutment between upper snap fit lips 68 of the push cap and upper inner flanges 34 of the chamber wall at the point 46a, or the second engagement mode referred above.

As further shown in FIG. 3E, during the use of the dispensing device when push cap 60 is further pressed downward until the low ends 63 of snap fit arms 62 are directly against stop platform 35 in the holding chamber, rim 74 of the piston head is disposed at line 47 in tubular member 40. This is the lowest point that rim 74 of the piston head can reach in the tubular member, therefore, this position of the spring loaded piston is referred to as injection ending position, and line 47 is also referred to as injection ending line. As shown in FIG. 3E, the injection ending position is controlled by the contact or abutment between the low ends 63 of snap fit arms 62 and stop platform 35 of the holding chamber at the point 47a.

The interior of proximal segment 44 of tubular member 40 is cylindrical. As described above, rim 74 of the piston head has a mating relationship with proximal segment 44 of the tubular member. The proximal segment 44 has a defined tubular volume between the injection starting line 46 and the injection ending line 47. The movement of the spring loaded piston from the injection starting position to injection ending position, in other words, the movement of the piston head 72 with its rim 74 from injection starting line 46 to injection ending line 47, displaces this defined tubular volume of air that is initially contained in the space between the injection starting and ending lines.

Optionally, holding chamber 30 further includes one or more vertical grooves to guide sliding movement of the push cap in the holding chamber. In the embodiment shown in FIGS. 3 and 3B, holding chamber 30 has two vertical grooves 39 disposed opposing each other. The lips 64 and 68 of the push cap are in mating relationship with grooves 39, and slide along grooves 39 when push cap 60 is pressed or released. As further shown in FIGS. 1 and 2, optionally holding chamber 30 may further comprises two opposing outer overhangs 37 as a gripping means for the user.

Figures 4, 5:
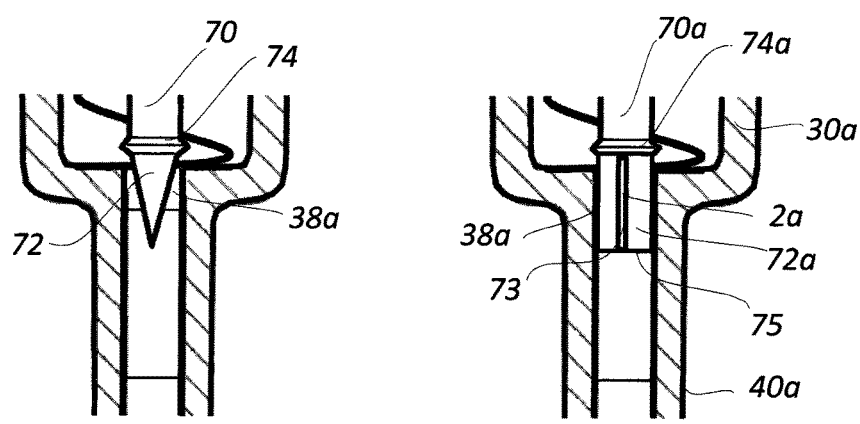
FIG. 4 is a partial cross sectional view of the dispensing device in an alternative embodiment of the present invention.
FIG. 5 is a partial cross sectional view of the dispensing device in a further alternative embodiment of the present invention.

FIG. 5 shows the structure of the piston head in an alternative embodiment. As shown, piston head 72a has a general cylindrical shape, and central opening 38a is straight without tapering shown in FIG. 3A. In this embodiment, piston head 72a has a venting recess 73 extending from rim 74a to distal end 75 of piston head 72a. The space 2a in the venting recess 73 is the venting space between the piston head and the central opening. At the venting position shown in FIG. 5, air communication between tubular member 40a and atmosphere through holding chamber 30a is established through space 2a in the venting recess 73.

Cannula 90 has a distal open end 92 and a proximal open end 94 that is affixed inside distal segment 42 of tubular member 40. The distal open end 92 of the cannula is sufficiently blunt to prevent needle sticking of a user, however, the cannula can penetrate the center of a rubber cap of a vacutainer commonly used in clinical laboratory. The cannula can be made of stainless steel or other suitable materials.

Figure 6:
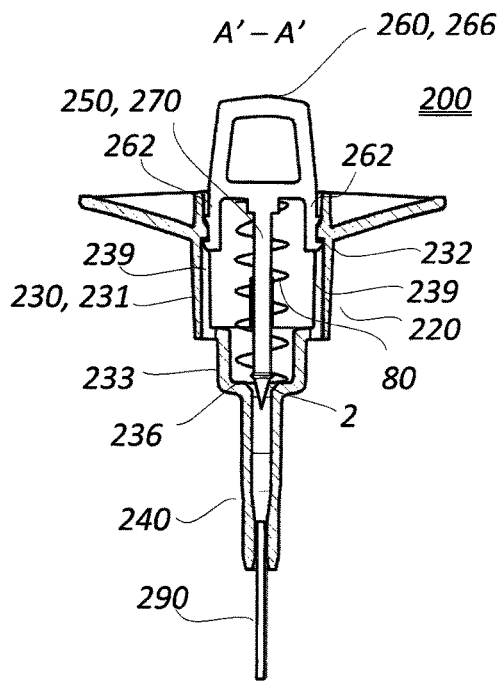
FIG. 6 is a cross sectional view of the dispensing device in a further embodiment of the present invention, along line A'-A' in FIG. 9, with the spring loaded piston at the venting position.

Now, referring to FIGS. 6 to 10, which show the structure of a dispensing device 200 in a further embodiment of the present invention. FIG. 6 shows a cross sectional view of the dispensing device, along line A'-A' in FIG. 9. As shown, dispensing device 200 comprises a housing 220, a spring loaded piston 250, and a cannula 290. Similar to that in dispensing device 10, housing 220 includes a holding chamber 230 with an upper chamber portion 231 and a lower chamber portion 233, and a tubular member 240 extending downward from bottom 236 of holding chamber 230 around central opening 238.

Figure 8:
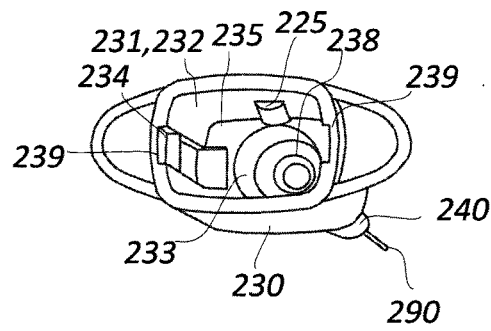
FIG. 8 is a top perspective view of the housing of the dispensing device shown in FIG. 6.
Figure 9:
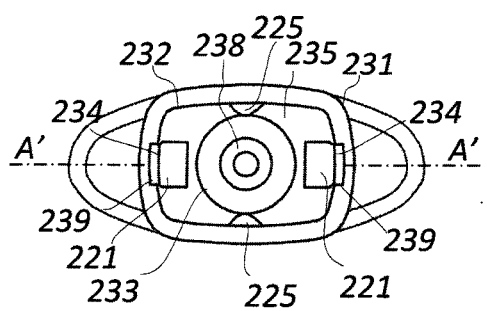
FIG. 9 is a top view of the housing of the dispensing device shown in FIG. 6.
Figure 7:
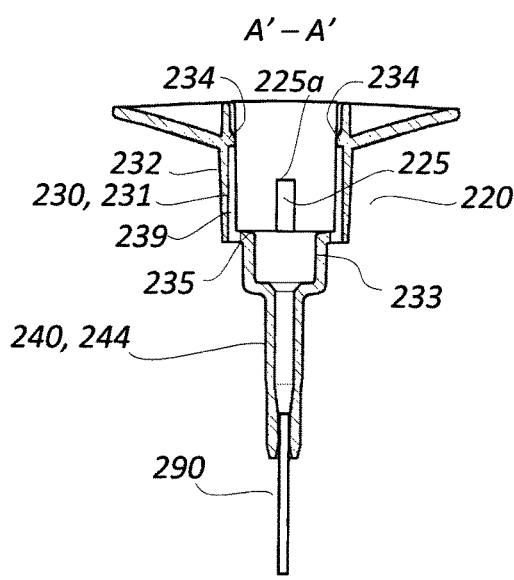
FIG. 7 is a cross sectional view of the housing of the dispensing device shown in FIG. 6, along line A'-A' in FIG. 9.

FIG. 7 shows a cross sectional view of housing 220. As shown, holding chamber 230 includes chamber snap fit elements on the inner side of chamber wall 232, in the form of a pair of chamber latches 234 disposed on opposing sides of the upper chamber portion. As shown in FIGS. 8 and 9, the upper chamber portion further includes two opposing vertical grooves 239, and each chamber latch 234 is formed within a vertical groove 239. Moreover, optionally holding chamber 230 further includes two through-holes 221 at the bottom of the upper chamber portion underneath vertical grooves 239. Through-holes 221 provide a convenient access for molding of the chamber latches 234.

Different from the embodiment shown in FIG. 3, in dispensing device 200 as shown in FIGS. 7 thru 9, holding chamber 230 further includes a pair of piston stops 225 disposed on opposing sides of the upper chamber portion, transverse to the direction of the pair of chamber latches 234. In the embodiment shown, each piston stop 225 is in a form of an elongated element protruding upward from bottom 235 of the upper chamber portion. Alternatively, piston stop may protrude from the chamber wall 232, without contact with bottom 235 of the upper chamber portion. Moreover, the piston stop may assume other shapes or forms as well as other positions in the upper chamber portion, so long as it inhibits the extent of vertical movement of the spring loaded piston in the holding chamber to control the injection ending position of the spring loaded piston. As can be seen in FIGS. 8 and 9, piston stops 225 are so positioned that they are away from the pathway of spring 80 when the spring is compressed or released from a compressed state during the use of the dispensing device. As can be further seen from FIG. 6, as well as FIGS. 3C-3D, the pathway of spring 80 is within the inner dimension of lower chamber portion 233.

Figure 10:
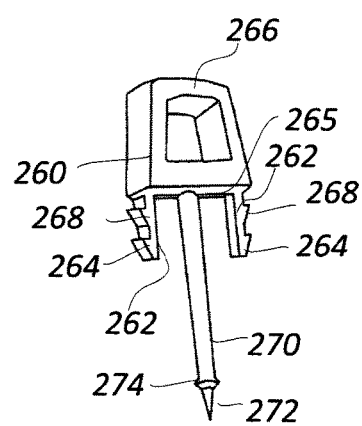
FIG. 10 is a perspective view of the spring loaded piston of the dispensing device shown in FIG. 6, with the spring removed.

As illustrated in FIGS. 6 and 10, spring loaded piston 250 includes a push cap 260, a piston rod 270 and a spring 80 with the same structural relationship described above in dispensing device 10. Piston rod 270 has a piston head 272 with a circumferential rim 274. The push cap 260 includes a top pusher 266 and two cantilever snap fit arms 262 extending downward from the underside 265 of top pusher 266. Each cantilever snap fit arm 262 includes a lower hook 264 and an upper hook 268 complementary to corresponding chamber latch 234 on each side of the chamber wall for snap fit connections with the respective chamber latch. The distance between lower and upper hooks 264, 268 is complimentary to the height of chamber latch 234 on chamber wall 232. The cantilever snap fit arms 262 with the lower and upper hooks 264, 268 are the snap fit elements of the push cap 260, and they assume the first and second engagement modes with the chamber latches 234 of the holding chamber 230 in the same manner described above in the dispending device 10 in reference to FIGS. 3C and 3D.

Figures 11, 11A, 11B:
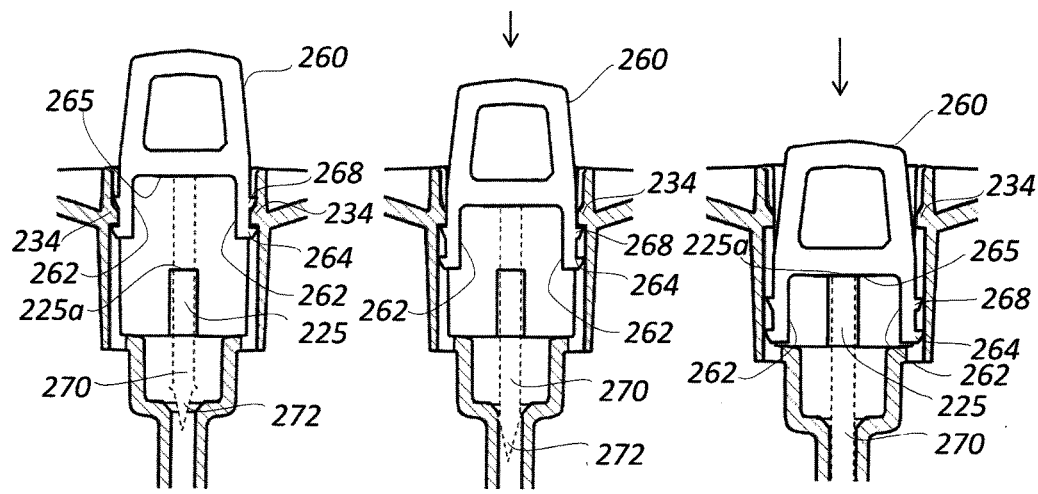
FIGS. 11-11B are enlarged partial cross sectional views of the dispensing device shown in FIG. 6, illustrating the first and second engagement modes between the arm snap fit elements of the push cap and the chamber snap fit elements of the holding chamber, and the abutment of the push cap with the piston stop at the injection ending position, respectively, wherein the spring is removed and the piston rod is in phantom to show the piston stop.

The structural features of dispensing device 200 that control the venting position, injection starting and ending positions of the spring loaded piston 250 are illustrated in FIGS. 11 thru 11B, wherein the spring is removed and the piston rod is in phantom for visual clarity of relevant elements. FIG. 11 shows the first engagement mode between the hooks 264, 268 of cantilever snap fit arms 262 of the push cap and chamber latches 234 of the holding chamber, which controls spring loaded piston 250 at the venting position as described above. This is the position of an assembled dispensing device before its use, wherein the lower hooks 264 have been irreversibly snapped over chamber latches 234, and abut against chamber latches 234 as driven by the force asserted by spring 80. Moreover, the upper hooks 268 are restricted by chamber latches 234 from moving downward in the absence of force applied by the user, so that the venting position of spring loaded piston 250 is maintained.

FIG. 11A shows the second engagement mode between the hooks 264, 268 of the cantilever snap fit arms 262 of the push cap and the chamber latches 234 of the holding chamber, which controls spring loaded piston 250 at the injection starting position as described above in reference to the dispensing device 10. At this position, the upper hooks 268 have been irreversibly snapped over chamber latches 234, however, the upper hooks 268 abut against chamber latches 234 as forced by spring 80, when no force is applied on the push cap by the user.

FIG. 11B shows spring loaded piston 250 at the injection ending position, which is controlled by the abutment of the underside 265 of top pusher 266 against the upper end 225a of piston stops 225 when the push cap is pressed down (see arrow) during transferring and dispensing a defined volume of a liquid as described hereinafter. In this embodiment, at the injection ending position of spring loaded piston 250, the lower ends of cantilever snap fit arms 262 are above through-holes 221, and are not in contact with the bottom 235 of the upper chamber portion of the holding chamber.

In dispensing device 200 shown in FIGS. 6 thru 10, one pair of chamber latches 234 are structured on the chamber wall for snap fit engagement with lower and upper hooks 264, 268 of cantilever snap fit arms 262 of the push cap. As can be readily understood, such a snap fit configuration can also be arranged in a reversed direction. For example, in an alternative embodiment of a dispensing device 300 shown in FIGS. 12-15, each cantilever snap fit arm 362 of pusher cap 360 includes one hook 364, while holding chamber 330 includes two sets of chamber latches 334a, 334b on the inner side of chamber wall 332 of upper chamber portion 331. As further shown in FIGS. 14 and 14A, chamber latches 334a, 334b on each side of the chamber wall are formed within a vertical groove 339. The distance between chamber latches 334a, 334b is complimentary to the height of hook 364. Such a reversed configuration also provides a cantilever snap fit engagement between the push cap and the holding chamber.

Figure 12:
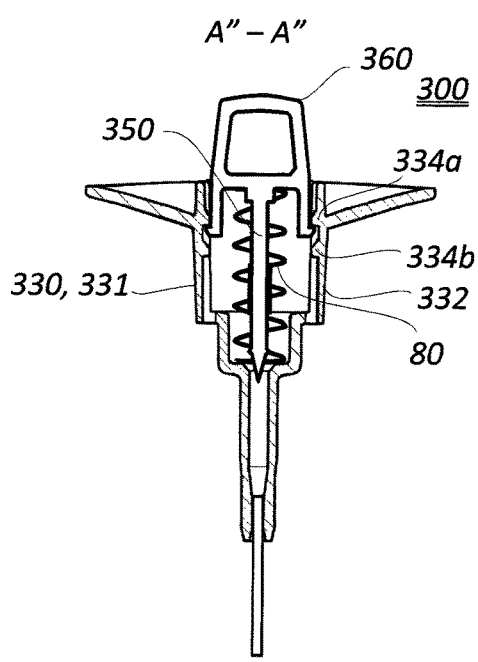
FIG. 12 is a cross sectional view of the dispensing device in a further alternative embodiment of the present invention, along line A"-A" in FIG. 14A, with the spring loaded piston at the venting position.

FIG. 12 shows the first engagement mode between the hooks 364 of cantilever snap fit arms 362 of the push cap and chamber latches 334a and 334b of the holding chamber, which controls spring loaded piston 350 at its venting position as described above. This is the position of an assembled dispensing device 300 before its use, wherein hooks 364 on the two cantilever snap fit arms 362 have been irreversibly snapped over chamber latches 334a, and abut against chamber latches 334a as driven by the force asserted by spring 80. Moreover, chamber latches 334b restrict hooks 364 from moving downward in the absence of force applied on the push cap by the user, so that the venting position of spring loaded piston 350 is maintained. In the second engagement mode, hooks 364 on the two cantilever snap fit arm 362 of pusher cap 360 have been irreversibly snapped over chamber latches 334b, however, the hooks 364 abut against chamber latches 334b as forced by spring 80, when no force is applied on the push cap by the user. Same as described above, the second engagement mode between the hooks on the cantilever snap fit arm of pusher cap and the chamber latches of the holding chamber controls the injection starting position of the spring loaded piston 350. In dispensing device 300 shown in FIGS. 12-15, the structures of piston stops 325 and lower chamber portion 333 of the holding chamber 330 are the same as those in dispensing device 200 described above.

Figure 14:
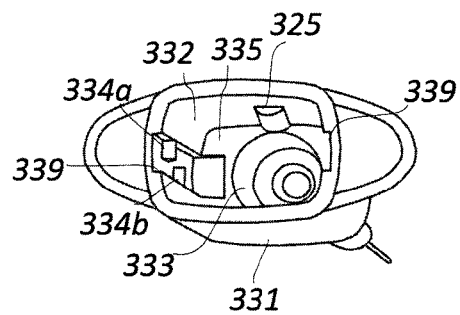
FIG. 14 is a top perspective view and FIG. 14A is a top view, respectively, of the housing of the dispensing device shown in FIG. 12.
Figure 14A:
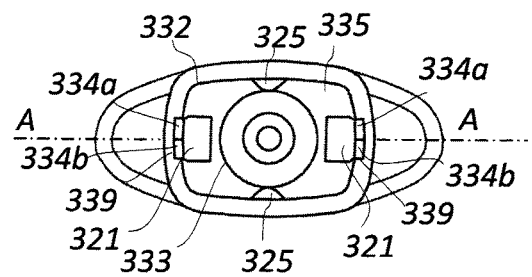
Figure 13:
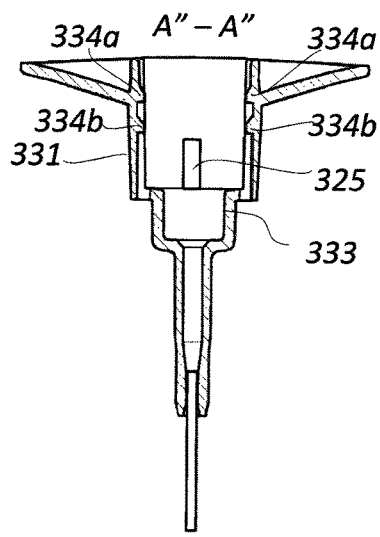
FIG. 13 is a cross sectional view of the housing of the dispensing device shown in FIG. 12, along line A"-A" in FIG. 14A.
Figure 15:
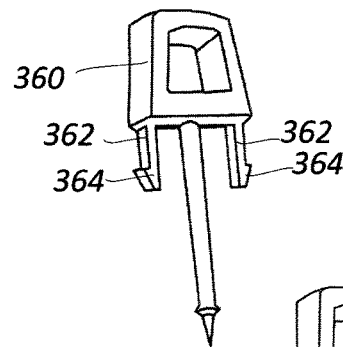
FIG. 15 is a perspective view of the spring loaded piston in the dispensing device shown in FIG. 12, with the spring removed.
Figure 16:
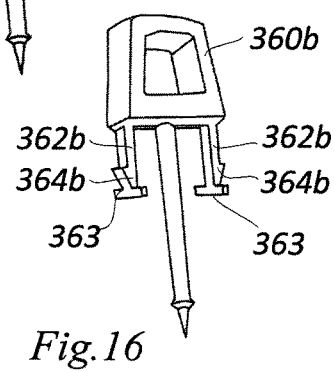
FIG. 16 is a perspective view of the spring loaded piston in an alternative embodiment, with the spring removed.

FIG. 16 shows a further alternative embodiment of a push cap 360b, which can be used with the holding chamber 330 of dispensing device 300 without the piston stops 325 shown in FIGS. 13-14A. As shown in FIG. 16, push cap 360b has two cantilever snap fit arms 362b and each has a hook 364b with the same structure of hooks 364 described above. Moreover, in this embodiment push cap 360b further includes a horizontal bar 363 at the lower end of each snap fit arm 362b. Horizontal bar 363 has a length beyond the width of through-holes 321 in the direction transverse to line A"-A" in FIG. 14A. In this embodiment, the bottom 335 of upper chamber portion 331 of the holding chamber function as a piston stop, similar to that described in the embodiment shown in FIG. 3. During the use of the dispensing device as described above, push cap 360b is pressed down until the horizontal bars 363 abut against the bottom 335 of the upper chamber portion 331 on both sides of through-holes 321, which establishes the injection ending position of the spring loaded piston.

Figures 17, 17A, 17B:
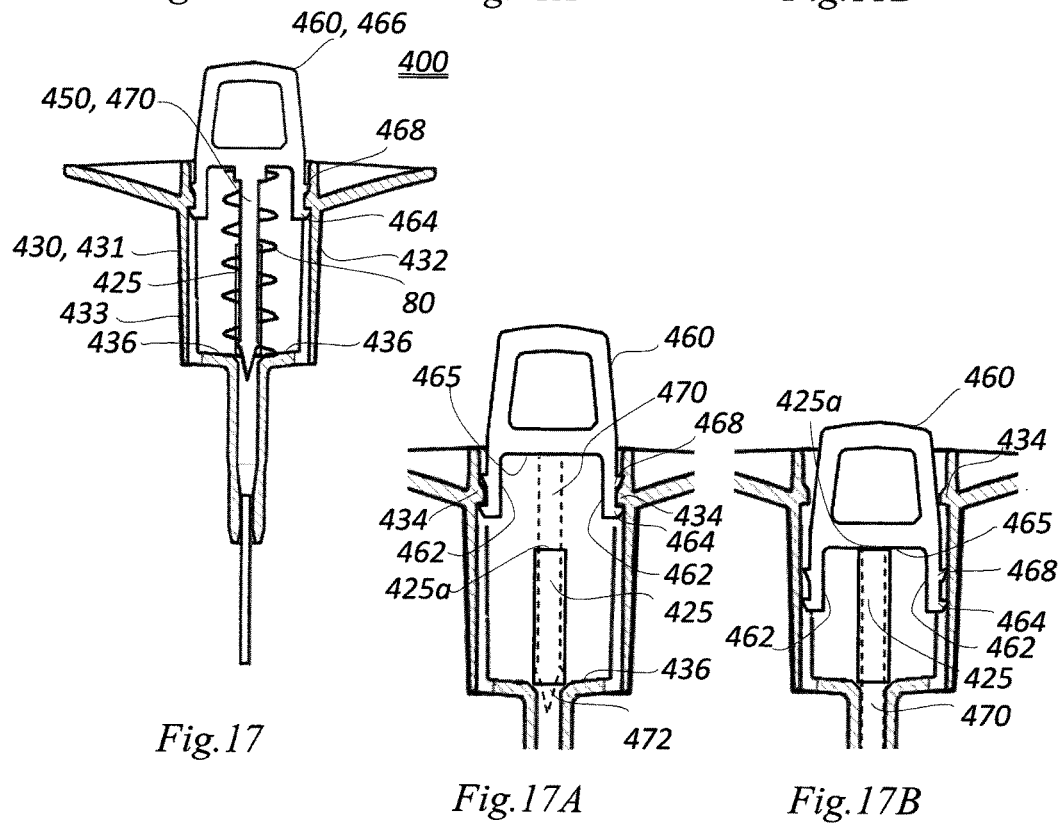
FIG. 17 is a cross sectional view of the dispensing device in an alternative embodiment of the present invention.
FIGS. 17A and 17B are enlarged partial cross sectional views of the dispensing device shown in FIG. 17, showing the spring loaded piston at the venting position and the injection ending position, respectively, wherein the spring is removed and the piston rod is in phantom to show the piston stop.

In the dispensing devices described above, optionally the lower chamber portion of the holding chamber has a smaller inner diameter than the upper chamber portion. FIGS. 17-17B illustrate a further embodiment of the present invention. As shown, in dispensing device 400 the upper chamber portion 431 and lower chamber portion 433 of holding chamber 430 have the same inner diameter. Similar to dispensing device 200 described above, dispensing device 400 includes a pair of piston stops 425 in the holding chamber. However, in the embodiment shown in FIGS. 17-17B, piston stops 425 are in the form of elongated elements protruding upward from bottom 436 of the holding chamber. As described above, alternatively the piston stops may assume other suitable shapes or forms. Other than the dimension of the upper and lower chamber portions and the position of piston stops 425, structural features of holding chamber 430 are the same as those in dispensing device 200 described above. FIG. 17A illustrates the spring loaded piston 450 at its venting position as controlled by the first engagement mode between the hooks 464, 468 of cantilever snap fit arms 462 of push cap 460 and chamber latches 434 on chamber wall 432 of the holding chamber as described above. FIG. 17B illustrates the spring loaded piston 450 at its injection ending position described above, as controlled by the abutment of the underside 465 of top pusher 466 against the upper end 425a of piston stops 425. The positions of piston head 472 of piston rod 470 at the venting position, injection starting and ending positions in relationship to tubular member 440 are the same as those described above in dispensing device 200.

The housing, push cap and piston rod can be made of plastics by plastic molding. Preferably, the housing has a single piece integral structure, which includes both the holding chamber and tubular member. The push cap and piston rod including the rim of the piston head of the spring loaded piston also preferably have a single piece integral structure. The cannula can be made of metal, such as stainless steel, glass, plastics or other suitable materials.

In a further embodiment, the present invention provides a method of using the dispensing device of the present invention described above for transferring a liquid from a closed container and dispensing a defined volume of the liquid.

FIGS. 18 thru 21 illustrate a process of using the dispensing device 10 as an example to transfer a blood sample from a vacutainer and to dispense a defined volume of the blood on a designated surface, such as a microscope slide. FIGS. 22 thru 26 further illustrate axial positions of the piston head in various steps during the blood transferring and dispensing process. The same transferring and dispensing process applies to dispensing devices 200, 300 and 400.

Figures 18, 19, 20:
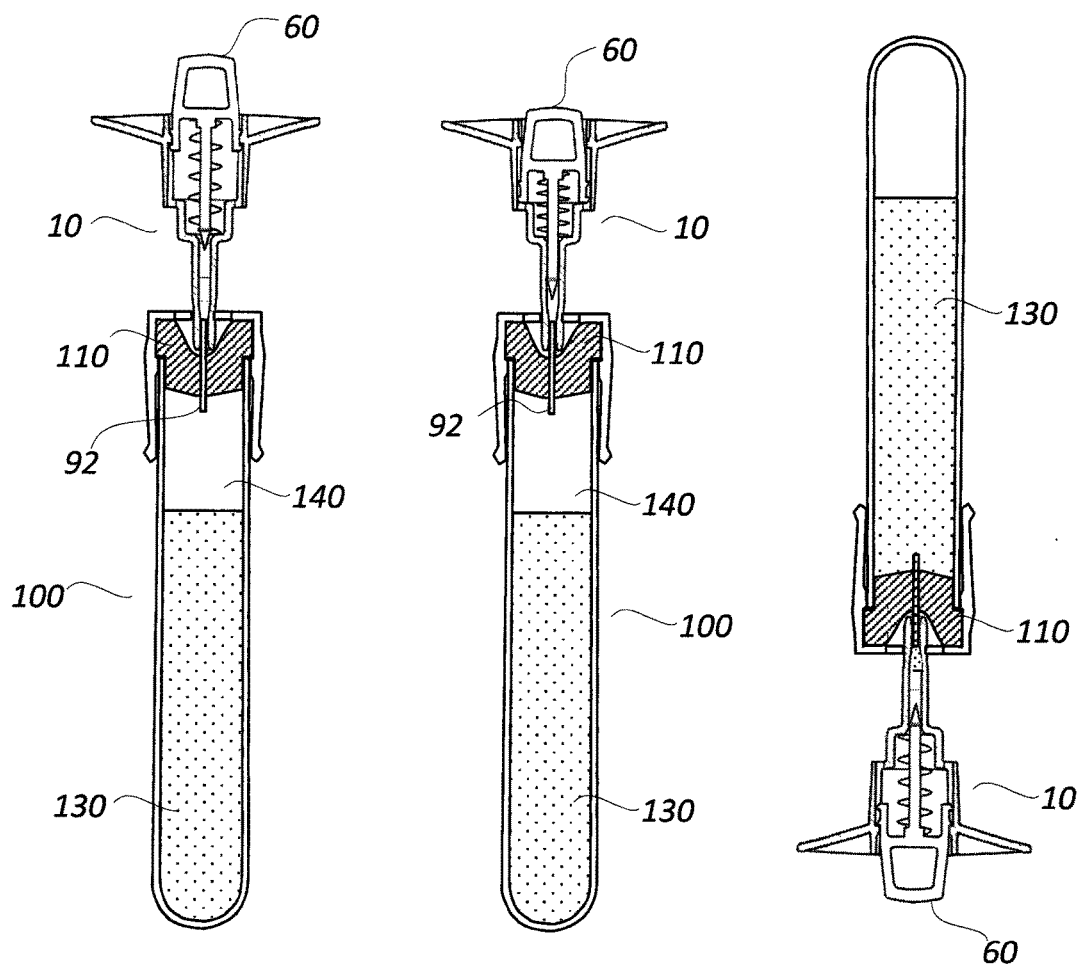
FIG. 18 is an illustrative cross sectional view of the dispensing device shown in FIG. 3 (or the dispensing device shown in FIG. 6) engaged with a vacutainer containing a blood at the beginning of a process of transferring and dispensing a defined volume of the blood from the vacutainer.
FIG. 19 is an illustrative cross sectional view of the dispensing device engaged with the vacutainer shown in FIG. 18, with the push cap pressed down and the spring loaded piston at the injection ending position.
FIG. 20 is an illustrative cross sectional view of the dispensing device engaged with the vacutainer shown in FIG. 18 in an upside down position, wherein the push cap is released and the blood is drawn into the cannula and the tubular member of the dispensing device.
Figures 22, 23, 24:
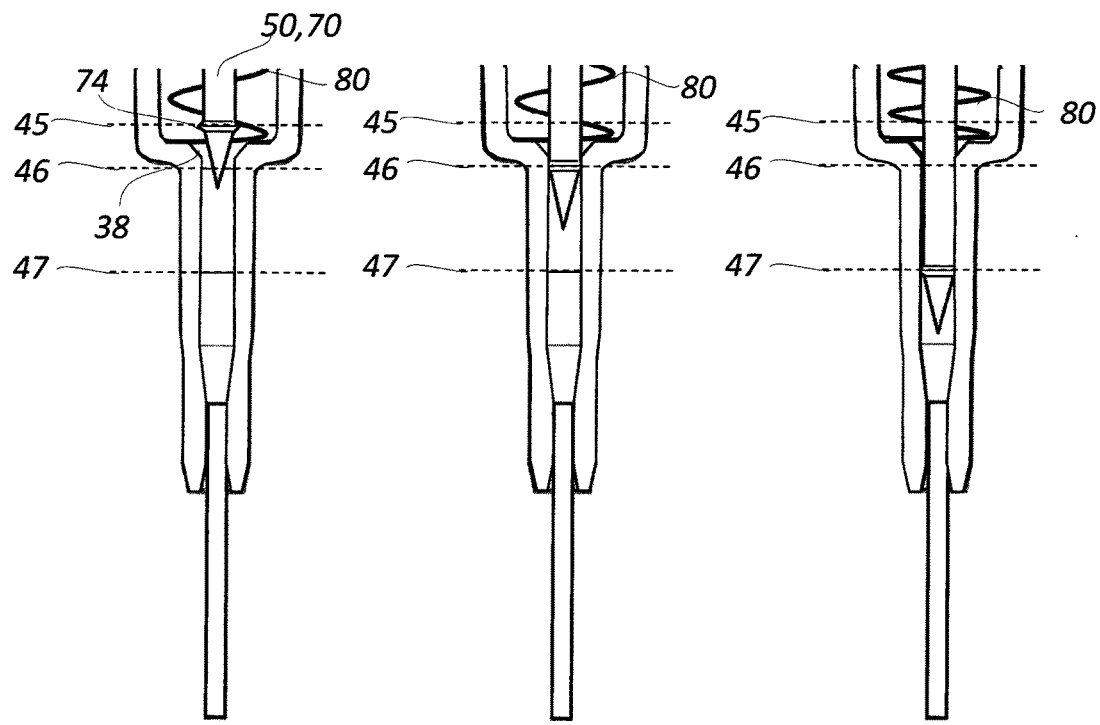
FIGS. 22-26 are enlarged illustrative partial cross sectional views of the dispensing device shown in FIG. 3 or FIG. 6, further showing the piston head of the spring loaded piston at various axial positions during the process of transferring and dispensing a defined volume of a liquid, wherein the cross sectional hatch lines are removed in order to show the line positions for visual clarity.

As shown in FIGS. 18 and 22, at the beginning of the process a user inserts cannula 90 of the dispensing device 10 into a vacutainer 100 through the center membrane of a sealing cap 110 while the spring loaded piston 50 is at its venting position. As described above, the venting position is controlled by the first engagement mode between snap fit elements of the push cap and chamber snap fit elements of the holding chamber (see FIGS. 3C and 18). As shown in FIG. 18, in this step both vacutainer 100 and dispensing device 10 are in a generally upright orientation. As shown, distal end 92 of the cannula is placed in a head space 140 above blood 130 contained in the vacutainer. As described above, at the venting position the rim 74 of piston head 72 situates at the venting line 45, and air communicates between the interior of tubular member 40 and external atmosphere through central opening 38 on the bottom of the holding chamber (see FIG. 22). As such, the internal pressure in the vacutainer is released through central opening 38. It should be understood that the internal pressure in a filled vacutainer before inserting dispensing device 10 can be either positive or negative. For a filled vacutainer that has not been opened, typically the internal pressure is slightly negative, and the internal pressure depends on the initial vacuum level of the vacutainer and the extent of filling of a blood sample, and varies tube by tube. On the other hand, once a filled vacutainer is opened by removing the sealing cap, the closing of the tube by pushing the sealing cap into the tube creates a positive pressure in the tube. However, when the dispensing device 10 is inserted in the vacutainer, after the venting through central opening 38 as described above, the air pressure in the vacutainer equalizes with the external atmosphere.

Then, push cap 60 is pressed down by the user until push cap completely stops moving further as shown in FIG. 19, in other words the spring loaded piston reaches the injection ending position. It is noted that when the push cap is pressed down, the upper snap fit lips 68 of the push cap are caused to irreversibly snap over the inner flanges 34 on chamber wall 32 first, then the push cap further slides down under the force asserted on the top pusher. As shown in FIGS. 22-24, when the push cap of the spring loaded piston is pressed downward from the venting position shown in FIG. 22, the rim 74 of the piston head first reaches injection starting line 46 as shown in FIG. 23. This closes the tubular member 40 and prohibits air communication between tubular member 40 and holding chamber 30. As such, further advance of the piston head from injection starting line 46 to injection ending line 47 as shown in FIG. 24 causes an injection into the vacutainer of a volume of air defined by the tubular volume between the injection starting line 46 and the injection ending line 47.

As shown in FIG. 19, distal end 92 of the cannula is disposed in the head space 140 above the blood in the vacutainer. Therefore, the defined volume of air from the dispensing device 10 is injected in the head space 140 without contacting the blood. If the cannula is placed into the blood to inject air, the risk of having an air bubble stuck on the cannula and subsequently entering the cannula when the blood is drawn into the dispensing device is high. Drawing the blood with the air bubble into the dispensing device could cause errors in the dispensed volume of the liquid.

Figures 25, 26:
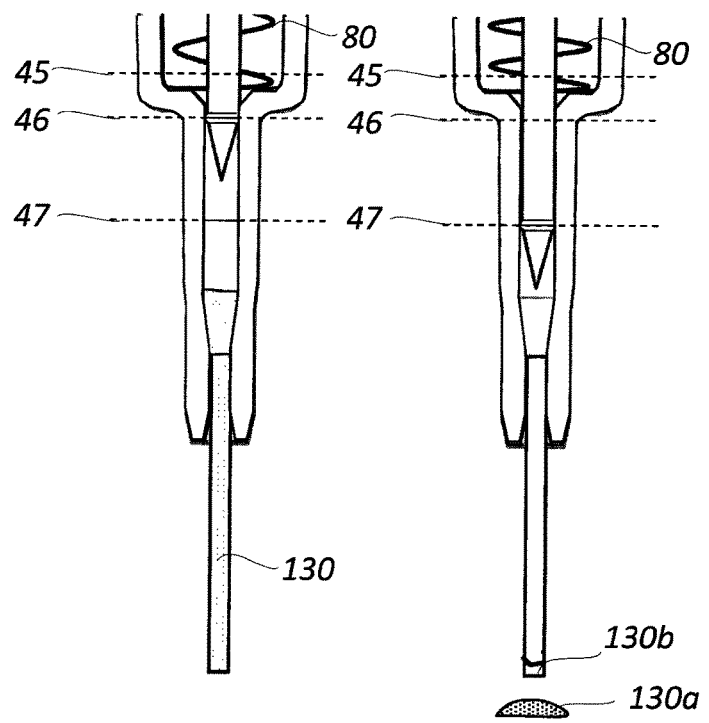

Then, vacutainer 100 together with dispensing device 10 are reversed to an upside down orientation, while keeping the push cap pressed down same as the position shown in FIG. 19. At this upside down orientation shown in FIG. 20, distal end 92 of the cannula is immersed in blood 130. Then, the force applied on the top pusher by the user is removed, push cap 60 automatically moves back as driven by the spring, as such the spring loaded piston returns to the injection starting position as shown in FIG. 25. This is the maximum extent that the spring loaded piston is able to return due to the restriction of upper snap fit lips 68 by the upper inner flanges 34 of the holding chamber, see FIG. 3D. As further shown in FIG. 20, at this time blood 130 enters into cannula 90 and distal segment 42 of the tubular member, mainly driven by a vacuum generated in tubular member 40 by the pull back of the piston head, and a known amount of blood is filled into the dispensing device. The blood flow can be visualized by the user.

Figure 21:
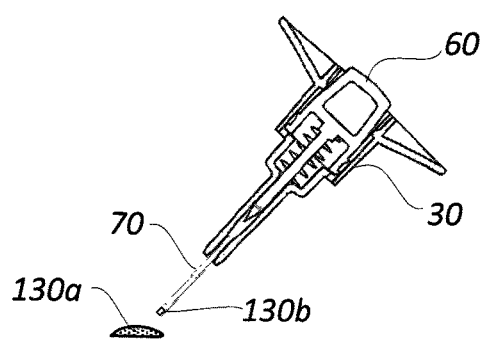
FIG. 21 is an illustrative cross sectional view of the dispenser, after dispensing a defined volume of the blood on a designated surface.

Then, the user withdraws the cannula of the dispensing device out of the sealing cap of the vacutainer, while keeping the spring loaded piston at the injection starting position same as that shown in FIGS. 20 and 25. It is noted that the injection starting position is automatically maintained by spring 80 in the absence of external force applied to the top pusher. After pulling out from the vacutainer, push cap 60 of the dispensing device is pressed down until it stops for dispensing the blood. As the push cap is pressed down as shown in FIGS. 21 and 26, the piston head advances from the injection starting line 46 to the injection ending line 47 and displaces a defined tubular volume of air downward as described above, which causes a volume 130a of the blood contained in the device being dispensed from the cannula. The dispensed volume 130a is quantitative and is equal to the defined tubular volume.

As further shown in FIGS. 21 and 26, a small residue portion 130b of the blood remain at the distal end of the cannula. The residue portion 130b have an effect of preventing air in the cannula being mixed into the dispensed volume 130a of the blood.

As an important and distinct feature, the dispensing device 10 can be used for transferring and dispensing the same liquid from the closed container for several times with a consistent volume. The process described above includes the first penetration of the vacutainer where an initial venting to release the internal pressure of the vacutainer takes place. In subsequent transferring and dispensing of a further portion of the liquid from the vacutainer, ventilation is no longer needed. The movement of the spring loaded piston will be only between the injection starting position and injection ending position described above. Therefore, the irreversible one time snapping over of the upper snap fit lips 68 with the upper inner flanges 34 of the chamber wall, corresponding to the change of the spring loaded piston from the venting position to the injection starting position, only occurs in the first transferring of the liquid from the vacutainer.

To dispense another defined volume of the blood from the same vacutainer, the force applied on the push cap is removed after dispensing the defined volume of the blood described above, and the spring loaded piston automatically resumes the injection starting position. This allows air entering in the tubular member from the cannula. Then, without pressing on the push cap, the cannula of the dispensing device is inserted again into the vacutainer with the vacutainer in the upright position. After the insertion, the push cap 60 is pressed down until the low end 63 of the push cap is against the stop platform 35, with the rim 74 of the piston head advancing from the injection starting line 46 to the injection ending line 47, which injects into the vacutainer again a volume of air defined by the tubular volume. Then, subsequent steps described above in reference to FIGS. 19-21 and 24-26 are repeated to dispense a second defined volume of the blood. Moreover, the same steps used for dispensing the second defined volume of the blood can be repeated to dispense the same defined volume of the blood from the same vacutainer multiple times.

As can be appreciated, the withdrawn volume of the blood from the vacutainer is substantially equivalent to the tubular volume of air injected into the vacutainer each time in the process of transferring and dispensing multiple defined volume of the blood. Therefore, the internal pressure in the vacutainer after the initial venting in the process of dispensing the first volume of blood remains substantially the same, despite multiple transfers of the blood from the same vacutainer. As such, the instant dispensing device can be used to dispense the same blood from the same closed tube for more than 10 times with a consistent defined volume.

It has been found that the method of using the instant dispensing device enables delivery of a defined volume of blood accurately and consistently. Such accuracy and consistency are not achievable with the existing blood dispensing devices. In an example of dispensing a blood sample of about 10 microliter (μl) in volume using the dispensing device 10 or 200, the percentage difference among multiple dispenses was ±5%. In comparison, the percentage difference using the Diff-Safe® blood dispenser (Alpha Scientific Corporation) by the same operator was ±40%. This demonstrates a significant improvement in precision in dispensing a blood sample using the dispensing device of the present invention.

Moreover, as an important feature of the present invention, the dispensed blood 130a is essentially free of air bubble. As can be appreciated from FIG. 20 and the transferring process described above, the distal end of the cannula is immersed in the blood before the external force on the push cap is released. This prevents introducing air bubble into the cannula when the blood enters into the cannula. Furthermore, for multiple transfer and dispenses, the interior surface of the dispensing device is wet with blood, which further reduces potential bubble formation on the interior surface of the dispensing device, and hence, enhances precision. Moreover, as described above a small residue portion of the blood remains at the tip of the cannula at the end of the dispensing, which has an effect of preventing air in the dispensing device being mixed into the dispensed volume 130a of the blood at the time of dispensing.

A dispensed blood sample free of air bubble is particularly advantageous. As described above, in preparing a blood smear on a microscope slide, air bubbles in a blood sample dispensed on the slide cause a disturbing bubble in the blood smear, and the slide has to be discarded and a replacement blood smear has to be prepared. Using the dispensing device and the method of the present invention, the number of blood smears can be effectively reduced due to elimination of frequent replacement preparation resulted from the interference caused by air bubbles, as well as less variation of blood volume.

The dispensing device of the present invention can be used for various applications where manual transferring and dispensing of a defined volume of a liquid from a closed container are needed. As described above, the dispensing device can be used for dispensing blood for preparing blood smears on microscope slides. The dispensing device is particularly suitable for providing a defined volume of blood or other biological samples for point-of-care diagnostic tests, such as for QuickRead diagnostic instruments from Orion Diagnostica, and other point-of-care instruments.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

The invention claimed is:

1. A dispensing device for dispensing a defined volume of a liquid, the dispensing device comprising:
   (a) a housing comprising:
      a holding chamber comprising an open top, a chamber wall having one or more chamber snap fit elements on an interior thereof, one or more piston stops, and a bottom with a central opening; and
      a tubular member extending downward from the central opening on the bottom of the holding chamber;
   (b) a cannula affixed to a distal segment of the tubular member; and
   (c) a spring loaded piston comprising
      a push cap disposed at least partially in the holding chamber, the push cap including a top pusher and at least one pair of snap fit arms extending downward from an underside of the top pusher; each of the snap fit arms including one or more arm snap fit elements complementary to the one or more chamber snap fit elements;
      a piston rod extending downward from the underside of the top pusher, coaxial with the central opening on the bottom of the holding chamber and the tubular member; and
      a spring disposed around the piston rod, with two opposing ends thereof against the underside of the top pusher and the bottom of the holding chamber, respectively;

wherein the dispensing device is configured that engagement modes between the one or more arm snap fit elements on the at least one pair of snap fit arms of the push cap and the one or more chamber snap fit elements of the holding chamber control a venting position and an injection starting position, respectively, of the spring loaded piston; and an abutment of at least one part of the push cap with the piston stop in the holding chamber controls an injection ending position of the spring loaded piston.

2. The dispensing device of claim 1, wherein in a first engagement mode between the one or more arm snap fit elements on the at least one pair of snap fit arms of the push cap and the one or more chamber snap fit elements of the holding chamber, the spring loaded piston is at the venting position wherein a piston head of the piston rod is so positioned that there is a venting space between the piston head and the central opening on the bottom of the holding chamber.

3. The dispensing device of claim 2, wherein in a second engagement mode between the one or more arm snap fit elements on the at least one pair of snap fit arms of the push cap and the one or more chamber snap fit elements of the holding chamber, the spring loaded piston is at the injection starting position wherein the piston head is situated in the tubular member immediately below the central opening on the bottom of the holding chamber, and the piston head prohibits air communication between the tubular member and the holding chamber.

4. The dispensing device of claim 2, wherein the piston head has a circumferential rim, and the outer diameter of the circumferential rim has a mating relationship with an inner diameter of a proximal segment of the tubular member.

5. The dispensing device of claim 4, wherein the proximal segment of the tubular member is cylindrical and has a defined tubular volume between the injection starting position and ending position of the spring loaded piston in the proximal segment of the tubular member.

6. The dispensing device of claim 1, wherein the abutment of at least one part of the push cap with the one or more piston stops in the holding chamber prohibits further advance of the piston rod in the tubular member.

7. The dispensing device of claim 1, wherein the one or more piston stops are in the form of one or more protruding elements with an upper end thereof disposed in an upper chamber portion of the holding chamber, and the injection ending position of the spring loaded piston is controlled by abutment of the underside of the top pusher against the upper end of the one or more piston stops.

8. The dispensing device of claim 1, wherein the holding chamber includes an upper and lower chamber portion, and the upper chamber portion includes the one or more chamber snap fit elements.

9. The dispensing device of claim 8, wherein the lower chamber portion has an inner diameter less than an inner diameter of the upper chamber portion, thereby forming a stop platform at a lower end of the upper chamber portion as the piston stop, and the injection ending position of the spring loaded piston is controlled by abutment of the snap fit arms against the stop platform at the lower end of the upper chamber portion.

10. The dispensing device of claim 1, wherein the holding chamber further includes one or more vertical grooves on the interior of the chamber wall, and the push cap slides along the one or more vertical grooves in response to a force applied thereon.

11. The dispensing device of claim 10, wherein the holding chamber further includes one or more openings on the bottom of the holding chamber underneath the one or more vertical grooves.

12. A method of transferring a liquid from a closed container and dispensing a defined volume of the liquid, said method comprising the steps of:
(a) obtaining a dispensing device that comprises
(i) a housing comprising a holding chamber comprising an open top, a chamber wall having one or more chamber snap fit elements on an interior thereof, one or more piston stops, and a bottom with a central opening; and a tubular member extending downward from the central opening on the bottom of the holding chamber;
(ii) a cannula affixed to a distal segment of the tubular member; and
(iii) a spring loaded piston comprising a push cap disposed at least partially in the holding chamber, the push cap including a top pusher and at least one pair of snap fit arms extending downward from an underside of the top pusher; each of the snap fit arms including one or more arm snap fit elements complementary to the one or more chamber snap fit elements; a piston rod extending downward from the underside of the top pusher, coaxial with the central opening on the bottom of the holding chamber and the tubular member; and a spring disposed around the piston rod, with two opposing ends thereof against the underside of the top pusher and the bottom of the holding chamber, respectively;
(b) inserting the cannula of the dispensing device into a closed container that is in an upright position while the spring loaded piston is at a venting position wherein a piston head of the piston rod is so positioned that there is a venting space between the piston head and the central opening on the bottom of the holding chamber, and placing a distal end of the cannula in a head space above the liquid contained in the closed container, thereby establishing an air communication between the closed container and atmosphere through the central opening to release an internal pressure in the closed container;
(c) then pressing on the top pusher to irreversibly depart from a first engagement mode between the one or more arm snap fit elements on the at least one pair of snap fit arms of the push cap and the one or more chamber snap fit elements of the holding chamber, and to advance the push cap until the at least one part of the push cap abuts against the piston stop, thereby causing the spring loaded piston to move from the venting position through an injection starting position to an injection ending position, and resulting in injection into the closed container of a volume of air defined by a tubular volume in the tubular member between the injection starting and ending positions of the spring loaded piston;
(d) turning the closed container and the dispensing device together to an upside down orientation while maintaining the push cap pressed down; and then releasing the push cap and allowing the push cap to pull back automatically with the spring loaded piston returning to the injection starting position, thereby drawing the liquid into the cannula;
(e) removing the cannula out of the closed container; and
(f) then pressing on the top pusher until the at least one part of the push cap abuts against the piston stop, thereby dispensing a defined volume of the liquid, wherein the defined volume of the liquid is the tubular volume between the injection starting and ending positions of the spring loaded piston in the proximal segment of the tubular member.

13. The method of claim 12, wherein the defined volume of the liquid being dispensed is substantially free of air bubble.

14. The method of claim 12 further comprising steps for dispending another defined volume of the liquid from the closed container:
- (g) releasing the push cap after step (f) and allowing air entering in the tubular member from the cannula;
- (h) inserting the cannula of the dispensing device again into the closed container that is in the upright position, without pressing the top pusher of the dispensing device;
- (i) then pressing on the top pusher until the at least a part of the push cap abuts against the piston stop, thereby causing the spring loaded piston to advance from the injection starting position to the injection ending position, and injecting into the closed container again of a volume of air defined by the tubular volume; and
- (j) repeating steps (d) to (f) to dispense another said defined volume of the liquid.

15. The method of claim 14 further comprising:
repeating steps (g) to (j) to further dispense said defined volume of the liquid from the closed container for multiple times.

* * * * *